(12) United States Patent
Sethi

(10) Patent No.: US 9,313,418 B2
(45) Date of Patent: Apr. 12, 2016

(54) METHOD AND APPARATUS FOR DETECTION OF BIOLOGICAL CONDITIONS

(71) Applicant: Toshiba America Electronic Components, Inc., San Jose, CA (US)

(72) Inventor: Rakesh Sethi, San Jose, CA (US)

(73) Assignee: Toshiba America Electronic Components, Inc., Irvine, CA (US)

( * ) Notice: Subject to any disclaimer, the term of this patent is extended or adjusted under 35 U.S.C. 154(b) by 246 days.

(21) Appl. No.: 13/905,413

(22) Filed: May 30, 2013

(65) Prior Publication Data

US 2014/0356966 A1 Dec. 4, 2014

(51) Int. Cl.

| | |
|---|---|
| *G01N 33/50* | (2006.01) |
| *H04N 5/247* | (2006.01) |
| *G01N 21/84* | (2006.01) |
| *G01N 21/21* | (2006.01) |
| *G01N 21/552* | (2014.01) |
| *A61B 5/00* | (2006.01) |

(52) U.S. Cl.
CPC ........ *H04N 5/247* (2013.01); *A61B 5/00* (2013.01); *G01N 21/21* (2013.01); *G01N 21/554* (2013.01); *G01N 21/84* (2013.01)

(58) Field of Classification Search
CPC ..... G01N 21/21; G01N 21/84; G01N 21/554; H04N 5/247
USPC .......................................... 436/86; 422/82.05
See application file for complete search history.

(56) References Cited

U.S. PATENT DOCUMENTS

| | | | |
|---|---|---|---|
| 6,607,387 B2 | 8/2003 | Mault | |
| 7,978,338 B2* | 7/2011 | De Groot et al. | ............. 356/497 |
| 8,031,335 B2 | 10/2011 | Wang et al. | |
| 2007/0015287 A1 | 1/2007 | Robbins et al. | |
| 2007/0258894 A1 | 11/2007 | Melker et al. | |

OTHER PUBLICATIONS

Early Diagnosis of Oral Cancer Based on the Surface Plasmon Resonance of Gold Nanoparticles; James Chen Yong Kah; et al.; International Journal of Nanomedicine; 2007.
Colloidal Gold—From Wikipedia, the free encyclopedia; http://en.wikipedia.org/wiki/Colloidal_gold dated Nov. 6, 2012.
Early Diagnosis of Oral Cancer Based on the Surface Plasmon Resonance of Gold Nanoparticles; James Chen Yong Kah; Kiawang Wei Kho, et al; Internationa Journal of Nanomedicine.

* cited by examiner

*Primary Examiner* — Rebecca M Fritchman
(74) *Attorney, Agent, or Firm* — Ulmer & Berne LLP

(57) ABSTRACT

A system and method for analysis of fluids, particularly bodily fluids such as saliva, uses an active, electrically-driven substrate for supporting an amalgamate of fluid and nanoparticles selected to adhere to one or more proteins. The nanoparticles affect light that is directed on or through the amalgamate. Different light directions, light polarization planes, and light wavelengths are used to obtain optical properties of the amalgamate. Once obtained, these values are compared to earlier or baseline values to determine a property of the amalgamate. Values or ranges are compared to earlier values, suitably with empirical association with maladies or conditions, to facilitate detection or diagnosis.

19 Claims, 3 Drawing Sheets

METHOD AND APPARATUS FOR DETECTION OF BIOLOGICAL CONDITIONS

TECHNICAL FIELD

The subject application includes embodiments directed generally to analysis of human conditions. Further embodiments include use of bodily fluids, such as saliva, for analysis and diagnostics of human conditions, including physiological states, such as possible maladies.

BACKGROUND

Assessment of physiological conditions is a fundamental aspect of diagnosis or treatment of diseases. Early assessments relied on direct human sensory input, including visual, aural, or taste. More recent advancements include use of tools such as x-rays, endoscopes, CT scanners, MRI scanners, PET scanners, genetic testing, ultrasound, chemical analysis, and pathogen testing to assess conditions in humans. The vast array of available tests greatly improves the ability to diagnose conditions accurately, providing a foundation from which available treatment options can be decided. While valuable, many of these tools are either expensive or time consuming to implement.

Current analysis techniques have evolved to include use of biological markers or biomarkers. Biomarkers serve as an indicator of normal biological processes, pathogenic processes, or pharmacologic responses. Biological markers may be used to associate with one or more human tissue or protein target. Once a target marker attaches to a site, the marker may be used to isolate targets of interest, such as by counting a number of markers as an indicator of the presence or absence of a particular protein of interest.

OVERVIEW OF EXAMPLE EMBODIMENTS

Figure 1:
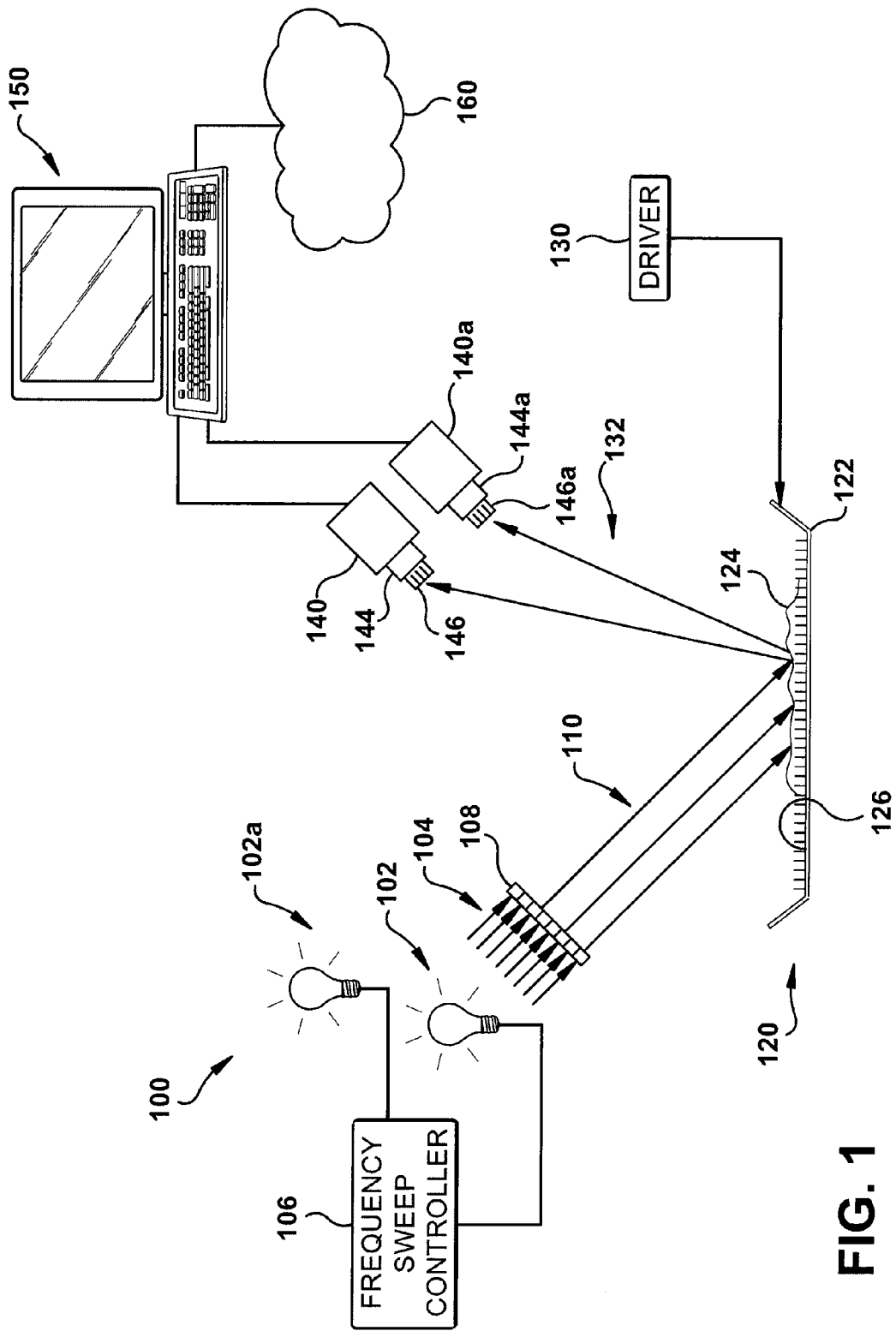
FIG. 1 illustrates an embodiment of an apparatus used in conjunction with the subject system and method for analysis of substances.

In accordance with an embodiment of the subject application, a system or method for analysis or diagnostics includes a memory operable to store baseline data corresponding to at least one optical baseline data acquisition. An active substrate receives a body sample/marker amalgamate, such as a saliva/nanoparticle amalgamate. A light generator directs light to the substrate to illuminate the amalgamate. Light that is either transmitted through or reflected from the amalgamate is directed to a camera system. The camera system, suitably a compound camera, receives light after exposure to the amalgamate. Light received by the camera system is used to generate corresponding optical data. The active substrate functions to generate an electric field, such as a collimated ion field, at the substrate by application of a voltage. A comparator generates comparison data relative to a comparison of optical data relative to baseline data that was previously stored. This comparison is used to generate an output corresponding to one or more properties of the amalgamate.

In accordance with another embodiment, a polarizer is placed between the light source and the amalgamate.

In accordance with another embodiment, the comparison data is representative of a shift in at least one of density, size changes, frequency, and bias associated with received light after reflection from the nanoparticles.

In accordance with another embodiment, the memory is further operable to store signature data representative of shifts associated with known protein signatures, and wherein the comparator is further operable to generate a diagnostic signal in accordance with a correlation of the signature data and the shift data.

In accordance with another embodiment, the comparator generates a diagnostic signal in accordance with correlation of the signature data with shift data associated with a plurality of amalgamate samples associated with a single, human subject.

In accordance with another embodiment, the nanoparticles are electro-reactive.

In accordance with another embodiment, the nanoparticles are comprised of gold or silver.

DESCRIPTION OF EXAMPLE EMBODIMENTS

In accordance with an embodiment of the subject application, illumination and light capture is accomplished to secure information about human conditions in a body fluid sample. In an example embodiment, a bio-markers that have light reflection or absorbing properties are used in connection with bodily fluids. In one embodiment, saliva is used. Saliva is advantageous insofar as it is quickly and painlessly obtainable. Saliva, given its relationship with the digestive system, including the stomach, esophagus, throat, mouth, etc., can carry valuable information relative to any of the bodily areas that affect it. While the descriptions herein include embodiments relative to analysis of saliva, it will be appreciated that the teachings herein are suitably implemented in connection with analysis of any bodily fluid, including blood, urine, lymph, etc. By way of further example, urine may provide indicators relative to issues associated with the kidneys, urethra, etc., as well as possible diseases associated with the areas of the body that influence the generation of urea.

Turning now to FIG. 1, illustrated is an embodiment of an analysis system 100 that includes a light source 102 that generates light 104. The light source 102 is suitably driven by a frequency/sweep controller 106. It will be appreciated that further embodiments suitably include two or more light sources, such as indicated by 102a. Multiple light sources provide additional functionality insofar as providing alternative light frequencies, either concurrently or over time, as well as providing for multiple angles of incoming light relative to an illuminated specimen as will be described in further detail below. The controller 106 enables generation of a selected range of light over a selected period of time. This light is suitably comprised of embodiments including a series of pulses or a continuous stream. The sweepable light source is suitably changeable between visible to infrared, such as with all or part of the wavelength range of 380 nm-1500 nm. The precise wavelengths used, and a duration of exposure to any particular wavelength area, is application specific and dictated by a property of a substance being viewed. By way of example, physical properties of certain proteins will cause them, when excited by influence of electromagnetic forces, such as electric fields or light, to unfold. When swept with certain wavelength and duration, there is provided an ability to target opening up (unfolding) of certain proteins to facilitate detection as described herein.

As will be detailed further below, embodiments of the subject application function by use of biological markers, and by exciting biological materials, such as proteins, into unfolding under conditions that maximize impact on detectable lighting properties. It will be appreciated by one of ordinary skill in the art that data from varying perspectives will afford additional information to facilitate detection and analysis. By way of example, additional information is suitably supplied by use of polarized light that facilities capture of light in one or more planes. In some embodiments, multiple camera angles or multiple lighting angles are suitably implemented to provide additional optical information.

Also illustrated in FIG. 1 is an optional polarizer 106. Polarized light 110 is suitably passed through polarizer 108 for polarization of light 104. A polarizer provides additional contrast and spatial information to an exposed specimen, which additional information allows for enhanced analysis capability.

Further illustrated in FIG. 1 is an analysis region 120, which is operable to receive light either directly, via a polarizer or at multiple angles from light source 102, which light is engineered in accordance with a particular analysis as noted above. Disposed in the region 120 is a substrate 122 operable to hold a sample 124 for illumination. In one embodiment, sample 124 is comprised of an amalgamate of a human fluid sample and a marker, such as a nanoparticle, as will described in greater detail below. In an embodiment of FIG. 1, the substrate 122 is suitably electro-reactive and formed with a series of engineered columns 126, such as being formed by a micro-electromechanical system ("MEMS"). As noted above, enhanced contrast is desirable to provide better data from which determinations of properties of substances is accomplished. A suitable MEMS substrate is electrically connected to a driver 130, power from which induces ionic current in the substrate. Such ionic current facilitates reaction with an associated substance, such as by providing for ion collimation channels therein. Such an alignment serves to provide further optical contrast in connection with the analysis described herein. In the illustrated embodiment, reflected light 132 emanates from sample 124 after exposure thereof to light from the light source 102 or sources 102 and 102a. It will be appreciated that, in addition to reflected light, data relative to the subject analysis system and method is also suitably achieved in connection with other specimen properties, including transmissibility, diffraction, or any other suitable electromagnetic affecting property.

After exposure to the specimen 124, light 132 is communicated to one or more light acquisition units, such as camera 140. As noted above in connection with light source 102 or sources 102 and 102a, two or more cameras, such as illustrated by cameras 140 and 140a, are advantageously implemented to provide light or image capture from multiple angles, multiple frequencies, different filters or polarizations, or the like, all of which suitably provides better contrast and hence better data for analysis in particular applications. With multiple angles, stereoscopic or three-dimensional information is made available. Any suitable camera, including CCD, CMOS, and the like are suitable for use in connection with the system and method detailed herein. A light field camera is advantageously used in certain applications, and bears an advantage of providing additional information for analysis of captured light relative to angles of light received.

Also illustrated in FIG. 1 are lenses 144, 144a, and filters or polarizers 146, 146a associated with cameras 140 and 140a, respectively. Captured data corresponding to images or light information from any camera is suitably communicated to a computing system for processing and analysis at computing system 150. The computing system 150 is suitably comprised of a digital computing system inclusive of at least one processor, data storage, input/output, and the like. The computing system 150 is also suitably connected for data interchange with a network 160, suitably comprised of one or more of a local area network (LAN), wide area network (WAN) or the Internet. Connection to one or more data devices facilitates data transfer for sharing, storage, collaboration or further analysis or comparison as will be appreciated by one of ordinary skill in the art.

In a representative embodiment, a biological substance for analysis is exposed to an imaging enhancing substance, such as a biological marker that will associate itself with a particular protein targeted for analysis. Embodiments herein include gold nanoparticles, silver nanoparticles, or any other suitable biological marker that can affect passage of light relative to a substance under analysis. Light-reflective particles, such as metallic particles, are particularly suited for the analyses taught herein. Accordingly, nanoparticles are not implemented as a biological marker in a conventional sense, but as a reflector to facilitate analysis of an effect on light after exposure. In a suitable embodiment, a camera, such as camera 140 in FIG. 1, suitably images up to a 1 mm strand of protein.

In the active substrate 122 of FIG. 1, a suitable voltage, up to 400 volts, is generated from the driver 130. Different proteins have different voltage dependencies, so particular voltages are application specific relative to a desired target. Proteins, such as that found in human bodily fluids, unfold depending on light wavelength, which wavelengths have different energy levels in accordance with the equation $E=hv$, where E is energy, h is Planck's constant, and v is frequency. Prior to lighting, proteins sit in a low energy level. Sweepable light source is suitably changeable from visible to infrared, basically in a range of wavelengths generally in the range of 380 nm-1500 nm. When swept with certain wavelength, one may suitably target opening up (unfolding) of certain proteins. Combinations of voltage and light/wavelength, both of which are known for a particular application event, provide corresponding information relative to light properties after exposure to a specimen. By way of example, large proteins will generally align electrically. In addition to electrical alignment of proteins for analysis, it will be appreciated that alignment is also suitably accomplished magnetically or with mechanical interaction, such as acoustically, thermally or ultrasonically. This suitably provides coagulation of labeled molecules to enhance light contrast properties.

When saliva is used as a specimen for analysis, it may advantageously include information relative to many types of oral or stomach cancers. In forming the amalgamate for analysis, any suitable, reflective nanoparticle is usable with saliva, including gold, silver, or composite. A selected type of nanoparticle is based on targeted proteins for detection or analysis. As noted above, these particles attach to proteins and are advantageously reflective so as to give a light signature that can be compared to earlier obtained and cataloged sample information so as to provide indicia relative to potential maladies.

A database of earlier information is suitably compiled and stored in a data storage, such as in a memory associated with the computing system 150, or a data device in network communication via network 160. This data is suitably accumulated by subjecting bodily fluids of patients with known conditions to the method or system noted herein. With sufficient data points and templates thus gathered, the earlier information provides an indicator or baseline, that may be compared, suitably by a hardware or software comparator in the computer system 150 or elsewhere in the data network 160, with a sample in order to detect or diagnosis conditions or diseases in a straightforward manner.

Figure 2:
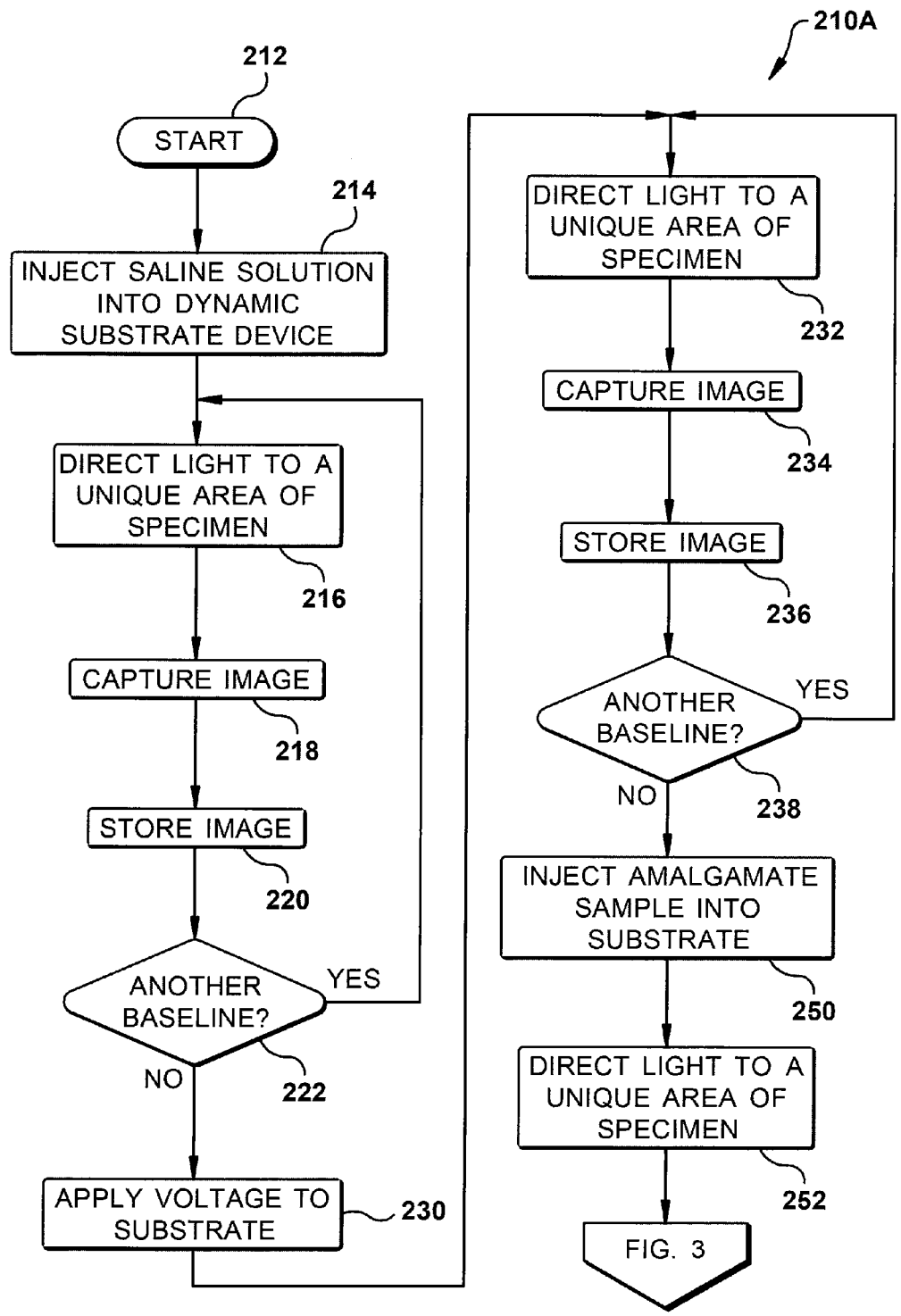
FIG. 2 is a flow diagram relative to an embodiment of the subject system and method for obtaining baseline data for analysis of substances.

Turning now to FIG. 2, with continued reference to FIG. 1, illustrated is an embodiment of a suitable process 210, portion 210A being referenced, to establish a baseline from which to accomplish the data acquisition and analysis detailed above, and subsequent detection and analysis, detailed above. Establishment of baseline values suitably commences at 212, progressing to step 214 wherein a baseline fluid, suitably saline solution with associated nanoparticles contained therein, is placed into viewing area 120 by disposing it on substrate 122. At block 216, light from the light source is directed to the solution, and images captured at block 218. The captured image is then stored in memory at block 220. Next, steps 216 through 222 are suitably completed multiple times to accumulate a working set of baseline values. Such additional baseline values are suitably obtained by directing the camera or cameras to different areas of the substrate.

Next, when a suitable number of initial baseline values have been obtained, progress is made to block 230, wherein a voltage is applied to the substrate on which the specimen is placed. Steps 232, 234, 236 and 238 are then completed for multiple image capture variations, analogously to acquisition of the baseline images in steps 216, 218, 220 and 222. Thus, stored baseline values include those associated with both an applied voltage and with no applied voltage.

Next, at block 250, a bodily fluid, suitably saliva, is placed on the substrate and illuminated at block 252. The saliva sample is suitably an amalgamate that includes suitable nanoparticles as noted above.

Figure 3:
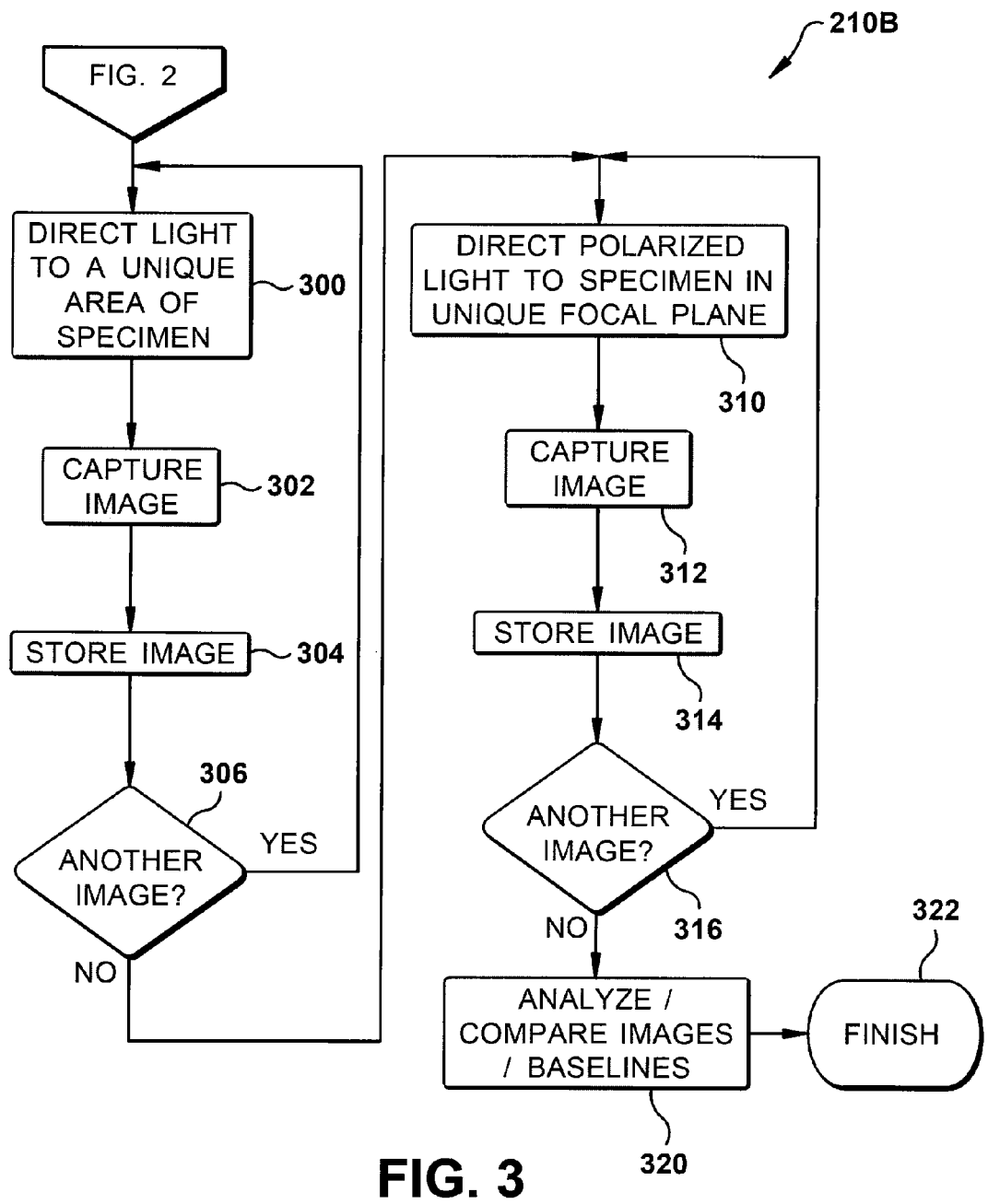
FIG. 3 is a further flow diagram relative to an embodiment of the subject system and method for obtaining fluid information and analyzing the same relative to baseline data.

Turning now to FIG. 3, the flow diagram of the process 210 of FIG. 2 is continued at 210B. Block 252 from FIG. 2 has been replicated for ease of reference. Steps 300, 302, 304, and 306 are then completed for multiple image capture variations, analogously to acquisition of the baseline images in steps 216, 218, 220 and 222, as well as the image acquisition steps 232, 234, 236 and 238. In this fashion, a first set of images associated with an actual human is obtained. That is to say, data associated with characteristics indicative of a physiology of a particular human subject has been obtained, and is now available for use in connection with detection or diagnosis of conditions, anomalies or maladies.

Next, progress is made to block 310 wherein the light source is provided with a polarizer as noted above. A sequence of image captures for each of a plurality of illumination angles, analogous to the capture sequences noted above, are obtained in connection with the polarized light in connection with blocks 312, 314 and 316.

Next, at block 320 images associated with the amalgamate are suitably compared via a comparator, software, or any suitable comparison system to earlier baseline data and corresponding characteristics associated therewith, and within tolerance or ranges as may be appropriate for a particular situation. Data from previously acquired, analyzed and categorized samplings suitably provides a base reference for such comparison and determination as will be understood by one of ordinary skill in the art. Such comparison yields diagnostic data associated with possible maladies or conditions associated with the fluid being analyzed. The process suitably terminates at block 322.

It is claimed:

1. A diagnostic device comprising:
    a memory configured to store baseline data corresponding to at least one optical baseline data acquisition;
    a substrate configured to receive a saliva/nanoparticle amalgamate;
    a light generator to direct light to the substrate to illuminate the amalgamate;
    a compound camera having a plurality of lenses configured to capture light from the amalgamate at multiple angles, the camera further configured to receive light from the light generator into each of the plurality of lenses after exposure to the amalgamate;
    the camera further configured to generate optical data corresponding to received light;
    a voltage generator configured to generate an electric field at the substrate;
    a comparator configured to generate comparison data corresponding to the optical data relative to stored baseline data; and
    an output configured to generate a signal in accordance with an output of the comparator.

2. The device of claim 1, further comprising a polarizer configured to polarize light from the light generator prior to illumination of the amalgamate.

3. The device of claim 2, wherein the comparator is further configured to generate the comparison data in accordance with shift data representative of a shift in at least one of density, size changes, frequency, and bias associated with received light after reflection from the nanoparticles.

4. The device of claim 3, wherein the memory is further configured to store signature data representative of shifts associated with known protein signatures, and wherein the comparator is further configured to generate a diagnostic signal in accordance with a correlation of the signature data and the shift data.

5. The device of claim 4, wherein the comparator is further configured to generate the diagnostic signal in accordance with correlation of the signature data with shift data associated with a plurality of amalgamate samples associated with a single, human subject.

6. The device of claim 1 wherein the nanoparticles are electro-reactive.

7. The device of claim 6 wherein the nanoparticles are comprised of at least one of silver, gold, and combinations thereof.

8. A diagnostic device comprising:
    an active, electro-reactive substrate configured for receiving an amalgamate comprising a human saliva sample with electro-reactive nanoparticles;
    a light source configured over a temporal sweep over selected range of light wavelengths, the light source being directed to the amalgamate;
    a camera configured to capture light from the light source after exposure thereof to the amalgamate;
    an image data generator configured to generate image data corresponding to the captured light, which image data includes data corresponding to an angle of captured light;
    a comparator configured to generate comparison data in accordance with a comparison of image data relative to stored baseline data; and
    an output generator configured to generate an output signal corresponding to an output of the generator.

9. The system of claim 8 wherein the active substrate is operative to generate an electromagnetic field across the amalgamate.

10. The system of claim 8 further comprising a sweep controller configured to selectively control a frequency range and time duration of the temporal sweep.

11. The system of claim 8 further comprising a polarizer disposed in an optical patch between the light source and the active substrate.

12. The system of claim 8 wherein the camera is further comprised of a compound camera having a plurality of lenses configured to capture light from the amalgamate at multiple angles.

13. A diagnostic device comprising:
- a memory configured to store baseline data corresponding to at least one optical baseline data acquisition;
- a substrate configured to receive a saliva/nanoparticle amalgamate;
- a light generator to direct light to the substrate to illuminate the amalgamate;
- a compound camera having a plurality of lenses configured to capture light reflected from the amalgamate at multiple angles, the camera further configured to receive light from the light generator into each of the plurality of lenses after exposure to the amalgamate;
- the camera further configured to generate optical data corresponding to received light;
- a voltage generator configured to generate an electric field at the substrate;
- a comparator configured to generate comparison data corresponding to the optical data relative to stored baseline data; and
- an output configured to generate a signal in accordance with an output of the comparator.

14. The device of claim 13, further comprising a polarizer configured to polarize light from the light generator prior to illumination of the amalgamate.

15. The device of claim 14, wherein the comparator is further configured to generate the comparison data in accordance with shift data representative of a shift in at least one of density, size changes, frequency, and bias associated with received light after reflection from the nanoparticles.

16. The device of claim 15, wherein the memory is further configured to store signature data representative of shifts associated with known protein signatures, and wherein the comparator is further configured to generate a diagnostic signal in accordance with a correlation of the signature data and the shift data.

17. The device of claim 16, wherein the comparator is further configured to generate the diagnostic signal in accordance with correlation of the signature data with shift data associated with a plurality of amalgamate samples associated with a single, human subject.

18. The device of claim 13 wherein the nanoparticles are electro-reactive.

19. The device of claim 18 wherein the nanoparticles are comprised of at least one of silver, gold, and combinations thereof.

* * * * *